US012778751B2

(12) United States Patent
Imbrie-Moore et al.

(10) Patent No.: US 12,778,751 B2
(45) Date of Patent: Nov. 3, 2026

(54) SELECTIVELY FLEXIBLE MITRAL ANNULOPLASTY DEVICES FOR OPTIMAL ANNULUS DYNAMICS AND BIOMECHANICS

(71) Applicant: THE BOARD OF TRUSTEES OF THE LELAND STANFORD JUNIOR UNIVERSITY, Stanford, CA (US)

(72) Inventors: Annabel M. Imbrie-Moore, Stanford, CA (US); Matthew Park, Piedmont, CA (US); Michael John Paulsen, Los Altos, CA (US); Y. Joseph Woo, Stanford, CA (US); Yuanjia Zhu, Stanford, CA (US)

(73) Assignee: The Board of Trustees of the Leland Stanford., Jr. University, Stanford, CA (US)

( * ) Notice: Subject to any disclaimer, the term of this patent is extended or adjusted under 35 U.S.C. 154(b) by 817 days.

(21) Appl. No.: 18/094,213

(22) Filed: Jan. 6, 2023

(65) Prior Publication Data

US 2023/0172716 A1 Jun. 8, 2023

Related U.S. Application Data

(63) Continuation of application No. PCT/US2021/041803, filed on Jul. 15, 2021.

(Continued)

(51) Int. Cl.
*A61F 2/24* (2006.01)

(52) U.S. Cl.
CPC .... *A61F 2/2448* (2013.01); *A61F 2250/0018* (2013.01)

(58) Field of Classification Search
None
See application file for complete search history.

(56) References Cited

U.S. PATENT DOCUMENTS

2003/0220686 A1 11/2003 Arru et al.
2005/0010283 A1 1/2005 Vijay
(Continued)

FOREIGN PATENT DOCUMENTS

EP 0595791 A2 5/1994
JP 2013009994 A 1/2013
(Continued)

OTHER PUBLICATIONS

Korean Intellectual Property Office, Authorized Officer Jung, Da Won, International Search Report for corresponding International Application No. PCT/US2021/041803, Nov. 3, 2021, 7 pages.

(Continued)

*Primary Examiner* — Tan-Uyen T Ho
(74) *Attorney, Agent, or Firm* — William A. English; Vista IP Law Group LLP

(57) ABSTRACT

Devices and methods are provided for mitral valve repair. For example, “C” or “D” shaped annuloplasty mitral valve rings are provided that include a structure including an elongate curved posterior segment and first and second curved lateral segments extending from opposite ends of the posterior segment, the posterior segment and lateral segments may lie within a plane and/or define a C-shape, the structure defining a first lateral axis extending between the lateral segments within the plane, and a second posterior-anterior axis perpendicular to the first axis intersecting a midpoint of the posterior segment, the structure having a stiffness such that the structure resists anterior-posterior motion along the second axis within the plane while allowing flexibility of the lateral segments out of the plane about the second axis.

19 Claims, 11 Drawing Sheets

Related U.S. Application Data

(60) Provisional application No. 63/052,366, filed on Jul. 15, 2020.

(56) References Cited

U.S. PATENT DOCUMENTS

| | | | | |
|---|---|---|---|---|
| 2005/0256569 | A1 | 11/2005 | Lim et al. | |
| 2011/0093065 | A1 | 4/2011 | Roberts | |
| 2013/0073031 | A1 * | 3/2013 | Brown | A61F 2/2466 623/2.11 |
| 2016/0045312 | A1 * | 2/2016 | Braido | A61B 5/02028 623/2.37 |
| 2019/0274830 | A1 | 9/2019 | Miller et al. | |

FOREIGN PATENT DOCUMENTS

| | | | | |
|---|---|---|---|---|
| WO | WO-2007136783 | A2 * | 11/2007 | A61B 5/061 |
| WO | 2011097251 | A1 | 8/2011 | |

OTHER PUBLICATIONS

Korean Intellectual Property Office, Authorized Officer Jung, Da Won, Written Opinion for corresponding International Application No. PCT/US2021/041803, Nov. 3, 2021, 8 pages.

European Patent Office, Extended European Search Report for corresponding Regional Application No. EP 21843326.6-1113, Nov. 7, 2024, 10 pages.

* cited by examiner

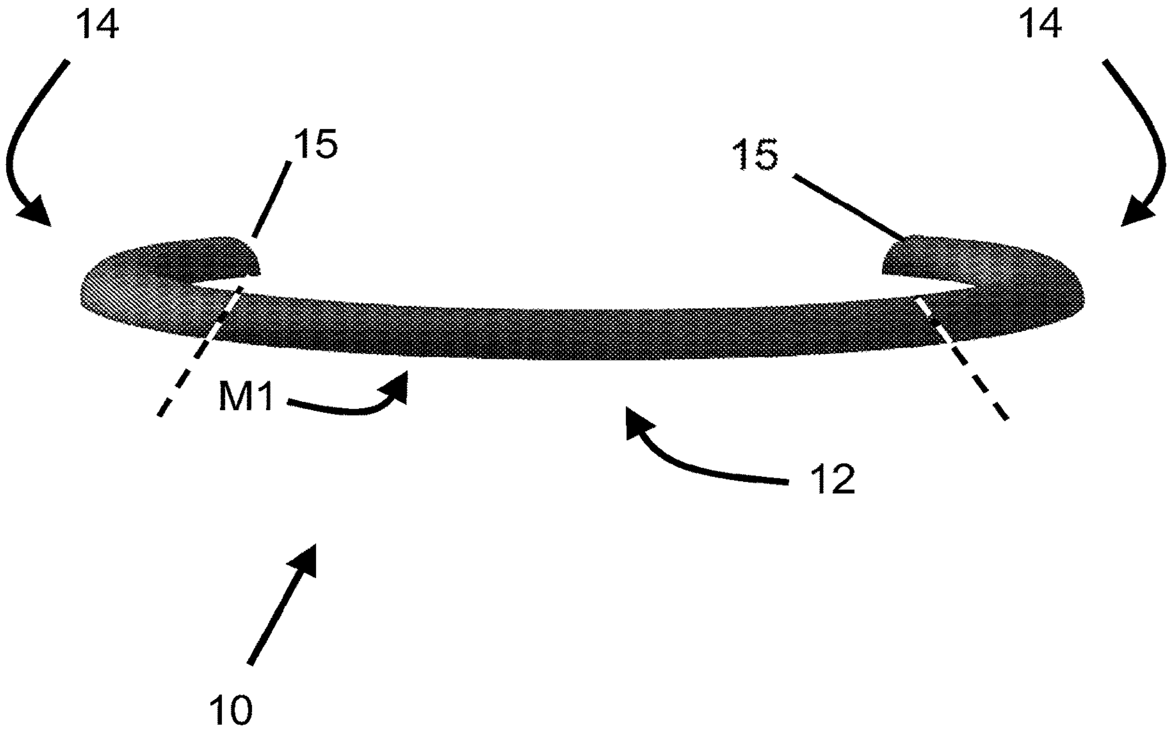
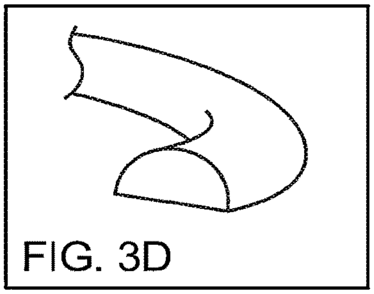
FIG. 3D
FIG. 3A

SELECTIVELY FLEXIBLE MITRAL ANNULOPLASTY DEVICES FOR OPTIMAL ANNULUS DYNAMICS AND BIOMECHANICS

RELATED APPLICATION DATA

The present application is a continuation of co-pending International Application No. PCT/US2021/041803, filed Jul. 15, 2021, which claims benefit of U.S. provisional application Ser. No. 63/052,366, filed Jul. 15, 2020, the entire disclosure of which is expressly incorporated by reference herein.

FIELD OF THE INVENTION

The present application relates to devices and methods for mitral valve repair, and, more particularly, to annuloplasty rings for mitral valve repair and methods for using them.

BACKGROUND

Mitral valve repair is one of the most common cardiac surgeries performed, encompassing more than 200,000 per year in the United States. An annuloplasty ring is a fundamental component in mitral valve repair. The annuloplasty ring functions to improve the size and/or shape of the annulus, prevent further annular dilation, and/or provide additional structural support. However, current mitral annuloplasty rings, including flexible, rigid, and semi-rigid rings, fail to simultaneously reduce the anteroposterior diameter while allowing for dynamic mitral annulus motion during cardiac cycles.

Mitral valves and annulus undergo conformational changes over the course of a cardiac cycle. When a semi-rigid or rigid annuloplasty ring is used in a valve repair to reduce the dimension of the annulus, this conformational change is restricted. Conversely, when a flexible annuloplasty ring is implanted that allows for this conformational change, the valve may also suffer from an inferior repair outcome due to a lack of rigidity holding the anterior and posterior segments of the annulus, which is associated with further annular dilation.

The rigid and semi-rigid rings currently on the market fix the mitral annulus to a predesigned shape, markedly reducing the mobility of the central posterior leaflet, so that the valve closure and competency is largely an anterior leaflet process. The flexible rings, although allowing some degree of motion of the mitral annulus, do not limit the degree of dilation in the anterior-posterior dimension, a feature in degenerative valve disease.

Therefore, improved devices for mitral valve repair would be useful.

SUMMARY

The present application is directed to devices and methods for mitral valve repair, and, more particularly, to annuloplasty rings for mitral valve repair and methods for using them.

In one example, a selectively, directionally flexible mitral annuloplasty ring is provided that meets the above-mentioned criteria: the design has the selective flexibility to allow the mitral annulus to transition between a substantially flat shape and a hyperbolic paraboloid shape (colloquially known as a "saddle" shape as used elsewhere herein) during the cardiac cycle while keeping a substantially fixed anterior-posterior annular dimension throughout the cardiac cycle. In another example, an annuloplasty ring is provided that includes slits of varying degrees of depth and separation in the central posterior portion of the ring and in the anterior portion of the ring between the two trigones. The varying degrees of depth and separation along the slits controls the degree of flexibility at each location along the ring as well as the three-dimensional geometry during the cardiac cycle. This directional slit design also prevents enlargement in the anterior-posterior dimension while still supporting significant flexibility in the specific directions and locations, which are required to allow for natural annular motion after the annuloplasty is performed. Optionally, casting may be used in the slit design, by replacing the anterior portion of the ring between the two trigones with flexible material to allow complete mobile motion of the anterior section to accommodate full aorto-mitral dynamics during a normal cardiac cycle.

In accordance with another example, an annuloplasty device is provided that includes a structure comprising an elongate curved posterior segment and first and second curved lateral segments extending from opposite ends of the posterior segment, the posterior segment and lateral segments lying within a plane to define a C-shape, the structure defining a first lateral axis extending between the lateral segments within the plane, and a second posterior-anterior axis perpendicular to the first axis intersecting a midpoint of the posterior segment, the structure having a stiffness such that the structure resists anterior-posterior motion along the second axis within the plane while allowing flexibility of the lateral segments out of the plane about the second axis.

In accordance with another example, an annuloplasty device is provided that includes a structure including an elongate curved posterior segment and first and second curved lateral segments extending from opposite ends of the posterior segment, the posterior segment and lateral segments lying within a plane to define a C-shape, wherein the lateral segments terminate in free ends opposite the posterior segment such that the device defines a generally "C" shape within the plane, the structure defining a first lateral axis extending between the lateral segments within the plane, and a second posterior-anterior axis perpendicular to the first axis intersecting a midpoint of the posterior segment, the posterior segment having a cross-section defining a maximum width parallel to the plane and a maximum height perpendicular to the maximum width, the maximum height being smaller than the maximum width to provide directional stiffness wherein the stiffness within the plane that is greater than the stiffness out of the plane such that the structure resists anterior-posterior motion along the second axis within the plane while allowing flexibility of the lateral segments out of the plane about the second axis.

In accordance with still another example, an annuloplasty device is provided that includes a structure including an elongate curved posterior segment; first and second curved lateral segments extending from opposite ends of the posterior segment, the posterior segment and lateral segments lying within a plane; and an anterior segment extending between ends of the lateral segments opposite the posterior segment, e.g., such that structure defines a generally "D" shape within the plane, wherein the structure defines a first lateral axis extending between the lateral segments within the plane, and a second posterior-anterior axis perpendicular to the first axis intersecting a midpoint of the posterior segment, and wherein the structure has a stiffness such that the structure resists anterior-posterior motion along the second axis within the plane while allowing flexibility of the lateral segments out of the plane about the second axis.

In accordance with yet another example, an annuloplasty device is provided that includes a structure formed from first material comprising an elongate curved posterior segment, and first and second curved lateral segments extending from opposite ends of the posterior segment, the posterior segment and lateral segments lying within a plane; and a substantially straight anterior segment formed from second material extending between ends of the lateral segments opposite the posterior segment, e.g., such that structure defines a generally "D" shape within the plane, wherein the structure defines a first lateral axis extending between the lateral segments within the plane, and a second posterior-anterior axis perpendicular to the first axis intersecting a midpoint of the posterior segment, and wherein the structure has a stiffness such that the structure resists anterior-posterior motion along the second axis within the plane while allowing flexibility of the lateral segments out of the plane about the second axis.

In accordance with still another example, an annuloplasty device is provided that includes a structure comprising an elongate curved posterior segment and first and second curved lateral segments extending from opposite ends of the posterior segment, the posterior segment and lateral segments defining a C-shape, the structure defining a first lateral axis extending between the lateral segments, and a second posterior-anterior axis perpendicular to the first axis intersecting a midpoint of the posterior segment, the structure having a stiffness such that the structure resists anterior-posterior motion along the second axis within the plane while allowing flexibility of the lateral segments out of the plane about the second axis.

In accordance with another example, a method is provided for performing annuloplasty that includes implanting an annuloplasty device within a patient's heart to a mitral valve annulus, the device comprising a posterior segment and lateral segments lying within a plane to define a C-shape, the device having a stiffness that resists anterior-posterior motion relative to the valve annulus while allowing flexibility of the lateral segments to follow movement of lateral regions of the valve annulus during normal operation of the heart.

Other aspects and features of the present invention will become apparent from consideration of the following description taken in conjunction with the accompanying drawings.

BRIEF DESCRIPTION OF THE DRAWINGS

The drawings illustrate examples of the invention, in which:

FIGS. 3A-3C show an example of a "C" shaped annuloplasty ring device including a posterior segment and lateral segments.

FIG. 3D is a cross-sectional detail of the device of FIGS. 3A-3C.

DETAILED DESCRIPTION

Figure 1:
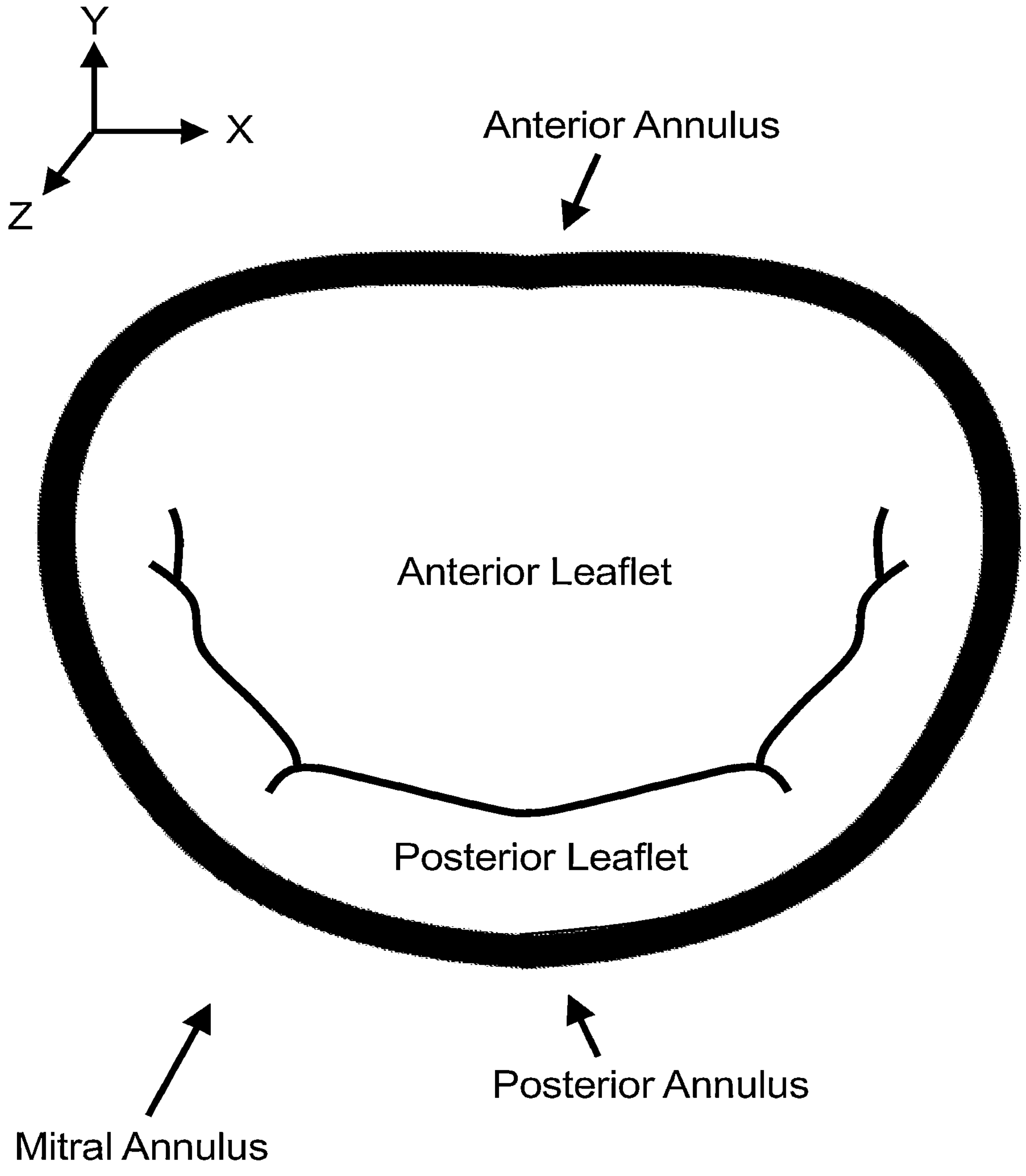
FIGS. 1 and 2 show the geometry of a typical mitral valve.

Before examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Examples of annuloplasty ring devices are provided herein that may exhibit selective flexibility to restrict anterior-posterior dilation, while allowing for conformational changes of the annulus during the cardiac cycle. Generally, the annuloplasty devices may include a structure including an elongate curved posterior segment and first and second curved lateral segments extending from opposite ends of the posterior segment, the posterior segment and lateral segments lying within a plane, the structure defining a first lateral axis extending between the lateral segments within the plane, and a second posterior-anterior axis perpendicular to the first axis intersecting a midpoint of the posterior segment. The structure may have a stiffness such that the structure resists anterior-posterior motion along the posterior-anterior axis within the plane while allowing flexibility of the lateral segments out of the plane.

In some examples, the lateral segments may terminate in free ends opposite the posterior segment such that the device defines a generally "C" shape within the plane. In other examples, the structure may also include an anterior segment extending between ends of the lateral segments opposite the posterior segment and lying within the plane, e.g., having a substantially straight or other configuration such that the device defines an enclosed asymmetrical ring shape, e.g., a generally "D" shape within the plane, similar to the shape of a native mitral valve. Alternatively, the device may have other partial or enclosed ring or band shapes, e.g., having a circular or oblong shape, which may correspond to other native heart valves.

In addition or alternatively, the devices may have a substantially flat or planar configuration in a relaxed state, e.g., such that the devices may be deformed from the planar configuration to accommodate movement of the valve annulus during the cardiac cycle while providing desired support of the valve annulus. Alternatively, the devices may have a saddle or other three-dimensional shape in its relaxed state.

Figure 3B:
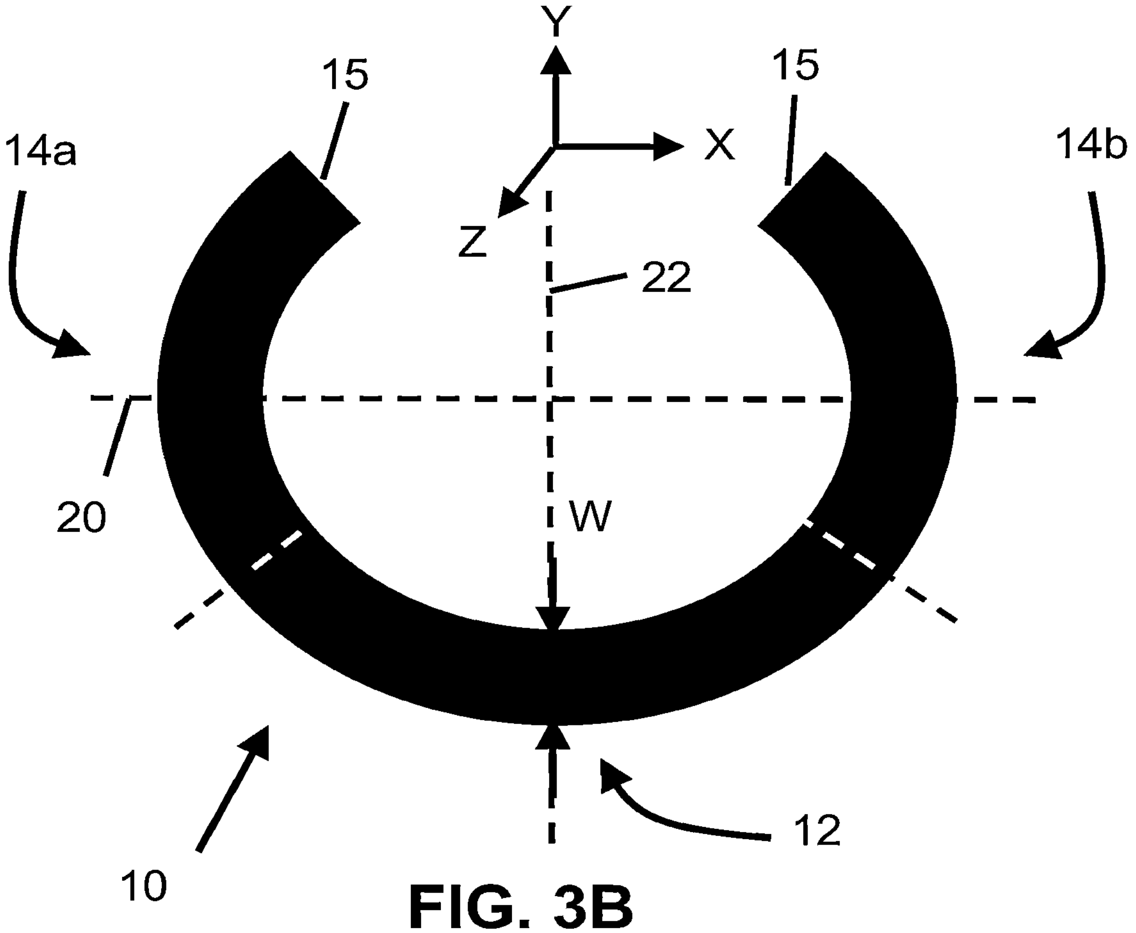
Figure 3C:
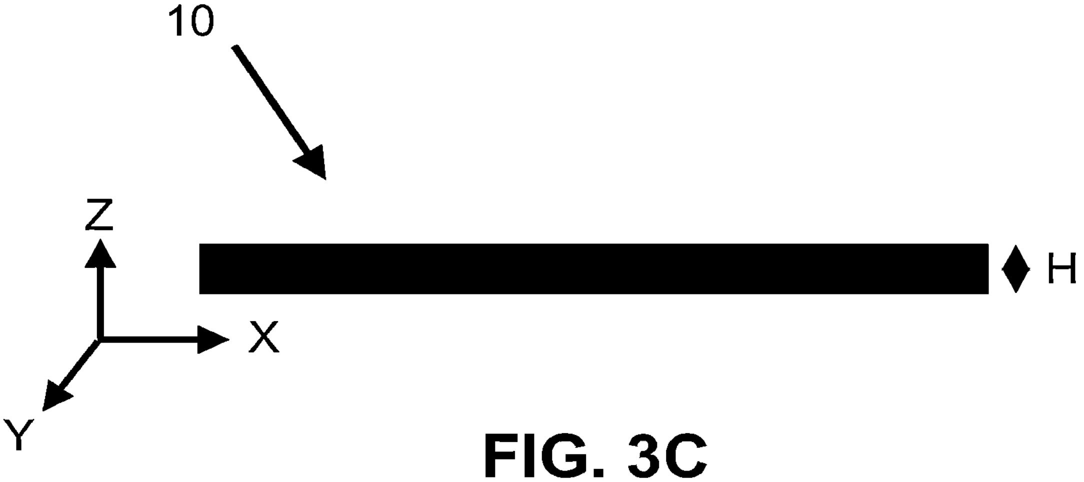

Turning to the drawings, FIGS. 3A-3C show an example of an annuloplasty ring or device 10 that includes a curved posterior segment 12 and first and second curved lateral segments 14 extending from opposite ends of the posterior segment 12 and terminating at anterior ends 15, thereby defining a generally "C" shape lying within a plane (e.g., within an X-Y plane as shown in FIG. 3B). As used herein, "lying within a plane" includes both a device that is flat in its relaxed state, i.e., where the posterior and lateral segments 12, 14 are completely parallel to and do not extend out of the X-Y plane, and a device that has a slight saddle shape in its relaxed state, e.g., where the lateral segments 14 may be lower than the midpoint of the posterior segment 12 relative to the X-Y plane. Thus, when viewed from above the X-Y plane, the device 10 "lying with a plane" projects a "C" shape (or alternatively a "D" shape in other examples herein) on the X-Y plane even if the lateral segments extend slightly out of the plane.

It will be appreciated that the segments 12, 14 may have a uniform or variable radius of curvature within the X-Y plane and still define a "C" shape as the term is used herein. For example, the posterior segment 12 may define a radius of curvature that is larger than the lateral segments 14. In addition, as shown, the lateral segments 14 may have the same radius of curvature and/or arc length, or alternatively, the lateral segments 14 may be shaped differently than one another, e.g., such that the device 10 has an asymmetrical "C" shape. For example, optionally, the right lateral segment 14*b* may have a larger radius of curvature and/or arc length than the left lateral segment 14*a* and/or the lateral segments may be otherwise shaped based on the anatomy of the native mitral valve annulus.

The device 10 may define a first lateral axis 20 extending between the lateral segments 14 within the X-Y plane (e.g., parallel to the X-axis shown in FIGS. 3B and 3C), and a second posterior-anterior axis 22 perpendicular to the first axis 20, e.g., intersecting a midpoint or centroid of the posterior segment 12 (e.g., aligned along the Y-axis shown in FIGS. 3B and 3C). In one example, the ratio of the overall height of the device 10 (along the second axis 22) to the overall width of the device 10 (along the first axis 20) may be about 3:4, although it will be appreciated that other dimensions and ratios may be provided as desired, e.g., to correspond to the intended anatomy valve annulus.

At least the posterior segment 12 has a cross-section defining a maximum width parallel to the X-Y plane ("W" shown in FIG. 3B) and a maximum height perpendicular to the maximum width ("H" shown in FIG. 3C), with the maximum height being smaller than the maximum width to provide directional stiffness such that the stiffness within the X-Y plane is greater than the stiffness out of the X-Y plane. In this manner, the device 10 may resist anterior-posterior motion along the Y-axis within the X-Y plane while allowing flexibility of the lateral segments 14 out of the X-Y plane, e.g., about the Y-axis. For example, as shown in FIG. 3D, the posterior segment 12 may have a semi-circular or less-than semi-circular cross-section, e.g., defining a flat surface parallel to the X-Y plane and an arc defining curved surface extending out of the X-Y plane along the Z-axis. Alternatively, the posterior segment may have other cross-sections, e.g., a rectangular, oblong, or other shape having a width W greater than the height H, e.g., to increase rigidity along the second axis 22 while providing flexibility out of the X-Y plane. In a further alternative, the posterior segment 12 may have partial flexibility within the X-Y plane, e.g., such that the lateral segments 14 may move away or towards one another along the first axis 20, while remaining substantially rigid along the second axis 22. In addition, different regions of the posterior segment 12 between the lateral segments 14 may have different flexibility. For example, one of the medial/lateral regions of the posterior segment 12 (i.e., the regions on either side of the midpoint) may have greater rigidity/flexibility than the other, e.g., by providing a smaller width and/or height along one of the regions than the other.

In this example, the lateral segments 14 have a cross-section similar to the posterior segment 12, e.g., such that the device 10 has a substantially uniform cross-section around the entire device 10, e.g., from the posterior segment 12 through to the anterior ends 15 of the lateral segments 14. As best in FIG. 3B, the anterior ends 15 may be substantially blunt, although, alternatively, they may have rounded or other shapes (not shown), e.g., to provide substantially atraumatic contact with tissue, e.g., of the native valve annulus.

Figure 5A:
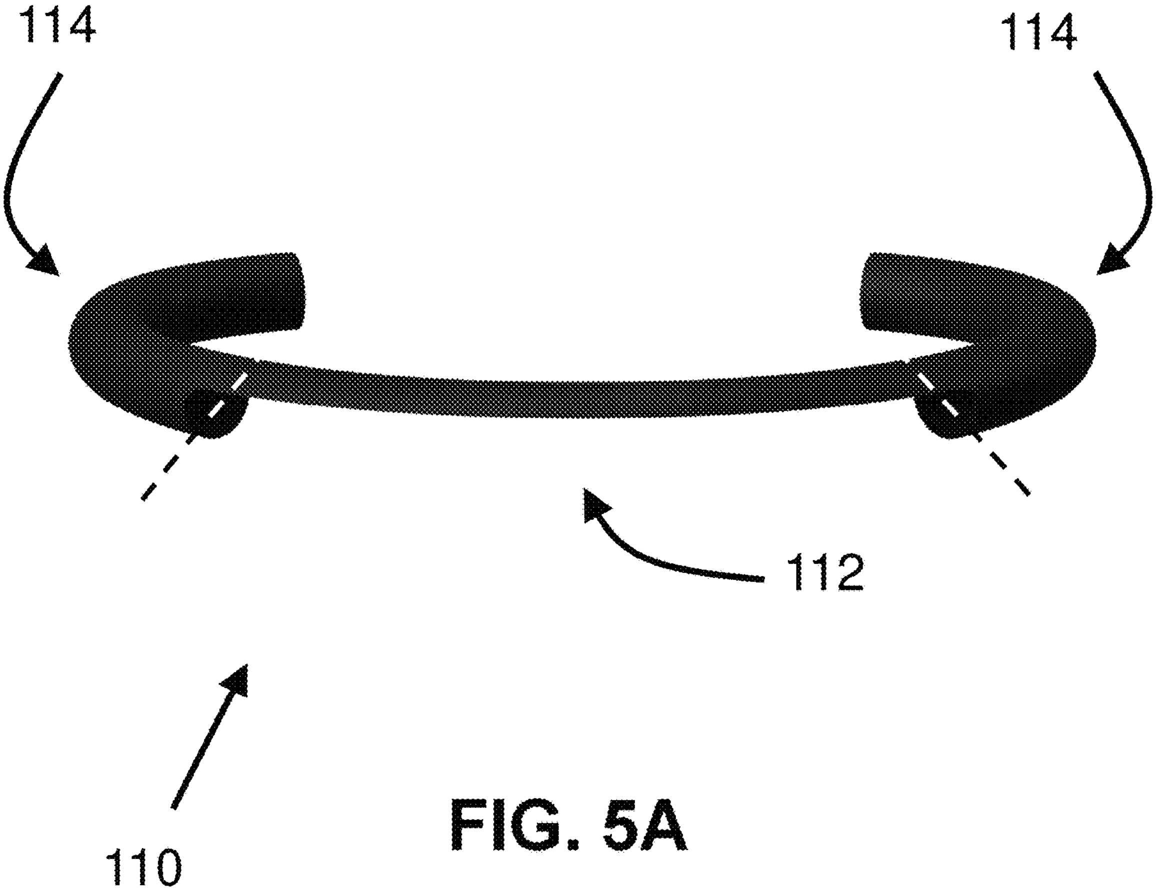
FIG. 5A shows another example of a "C" shaped annuloplasty ring device.

Alternatively, as shown in FIG. 5A, an annuloplasty ring device 110 may be provided that includes lateral segments 114 having a cross-section greater than the posterior segment 112. In this alternative, the lateral segments 114 may have a substantially circular or oblong cross-section while the posterior segment 112 has a semi-circular cross-section, which may increase rigidity of the lateral segments 114 relative to the posterior segment 112. Thus, the configuration of the lateral segments 114 may enhance resisting movement along the posterior-anterior axis 22 within the X-Y plane, while the posterior segment 112 accommodates movement of the lateral segments 114 out of the X-Y plane, e.g., to adopt a saddle shape, e.g., similar to mitral valve shown in FIGS. 1 and 2.

Figure 4:
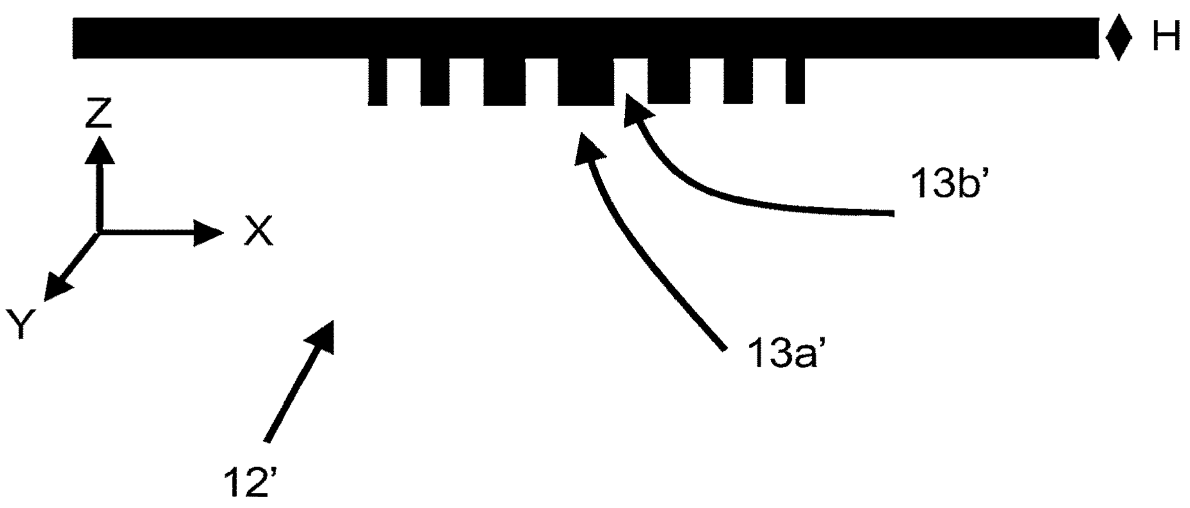
FIG. 4 is a detail showing examples of kerfing that may be provided on a posterior segment of an annuloplasty ring device, such as that shown in FIGS. 3A-3D.
Figure 5B:
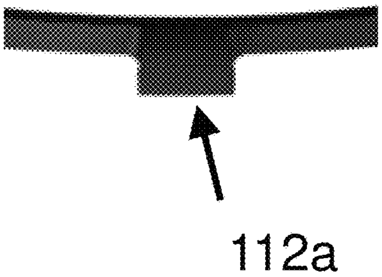
FIG. 5B is a detail of the device of FIG. 5A showing an optional raised or thickened region that may be provided on a posterior segment of the device.

In addition or alternatively, with continued reference to FIGS. 3A-3C, the device 10 (or any of the other devices herein) may include one or more features to modify the stiffness of segments of the device 10 and/or limit movement. For example, as shown in FIG. 4, an alternative posterior segment 12' is shown that includes a variable thickness (i.e., height "H" along the Z-axis), i.e., perpendicular to the X-Y plane. In the example shown, the posterior segment 12' has a plurality of relatively thick regions 13*a*' separated by thinner regions 13*b*', which may facilitate bending of the posterior segment 12' out of the X-Y plane. For example, the posterior segment 12' (or optionally other segments of the devices herein) may be kerfed or grooved, i.e., may include multiple relatively thin slots 13*b*' formed therein that decouple adjacent relatively thick regions 13*a*' to provide increased flexibility while limiting motion out of the X-Y plane. In essence, given the rigidity modulus of the base material of the posterior segment 12', the kerfing or grooves may selectively reduce the resulting stiffness of the posterior segment 12'. Alternatively, as shown in FIG. 5B, a single relatively thick region 112*a* may be provided, e.g., at a midpoint of the posterior segment 112, and regions between the midpoint and the lateral segments may have a substantially uniform, relatively thinner height, e.g., similar to posterior segment 112 shown in FIG. 5A.

Returning to FIGS. 3A-3C, the segments 12, 14 of the device 10 may be integrally formed together, e.g., from the same material, for example, by one or more of molding, casting, 3D-printing, and the like. The device 10 may be formed from biocompatible materials, such as plastic material, e.g., silicone, urethane, polyurethane, polyethylene, and the like, metal material, e.g., Nitinol, Elgiloy, and the like, or composite materials. In one example, the device may be formed from plastic material having a Shore hardness ranging from 10 A to 40 A.

Optionally, the device 10 may include one or more regions or segments attached to the posterior segment 12 and/or lateral segments 14, e.g., to modify the stiffness of the regions and/or to provide a desired shape or finish to the device. For example, for the device 110 shown in FIG. 5A, an optional soft material (not shown) may be attached to the posterior segment 112, e.g., by co-molding, bonding, fusing, and the like, to provide a desired outer profile, e.g., a circular or oblong cross-section (not shown) similar to the lateral segments 114, such that the final device 10 has a substantially uniform shape, similar to other devices described elsewhere herein.

In addition, one or more pieces of fabric or polymer, e.g., formed from polyester, polyethylene terephthalate (PET), and/or other materials), may be applied around the device 10 (and any of the other devices herein), e.g., wrapped around or otherwise covering exposed surfaces and/or stitched together to provide a finished annuloplasty ring. Optionally, an outer coating or layer of relatively soft and/or flexible material, e.g., silicone, may be wrapped or attached around the outer surface of the device 10 (or any of the other devices herein) before applying a fabric wrap, which may facilitate implantation of the device 10. Thus, the inner structural material of the device 10 may be covered with soft and/or flexible material that is, in turn, surrounded by fabric.

Optionally, the fabric material properties may be selected to be slightly elastic such that if a transcatheter mitral valve replacement occurs after this annuloplasty ring is implanted, the ring could break under the expansion force during the replacement without ripping the fabric. Any component of the ring material may be designed to be breakable if desired for future intervention. Additionally, MRI-compatible materials that may be seen under fluoroscopy or X-ray may be used in the device in order to facilitate future interventions.

Optionally, a sewing cuff (not shown) of material that may be punctured with a suture (i.e., fabric or a polymer) may be incorporated into the device 10 (or any of the other devices herein) and/or attached around all or a portion of a perimeter of the device to facilitate the repair procedure. For example, a cuff may be provided that at least partially surrounds the device or resides on the inner, outer, top, and/or bottom regions of device. Optionally, the sewing cuff or outer fabric may be marked with colors to indicate the separation between the sewing cuff and the more rigid sections of the device. The outer fabric may also use colors to indicate useful landmarks on the device, for instance, the commissures, trigones, and midline of the anterior or posterior segments. Optionally, any of the devices herein may include one or more loops, holes, or other features formed in or attached to the fabric, e.g., a plurality of loops or holes spaced apart from one another around the perimeter of the devices, sized to receive a needle and/or sutures, to facilitate anchoring the device relative to the native valve annulus.

Figure 6A:
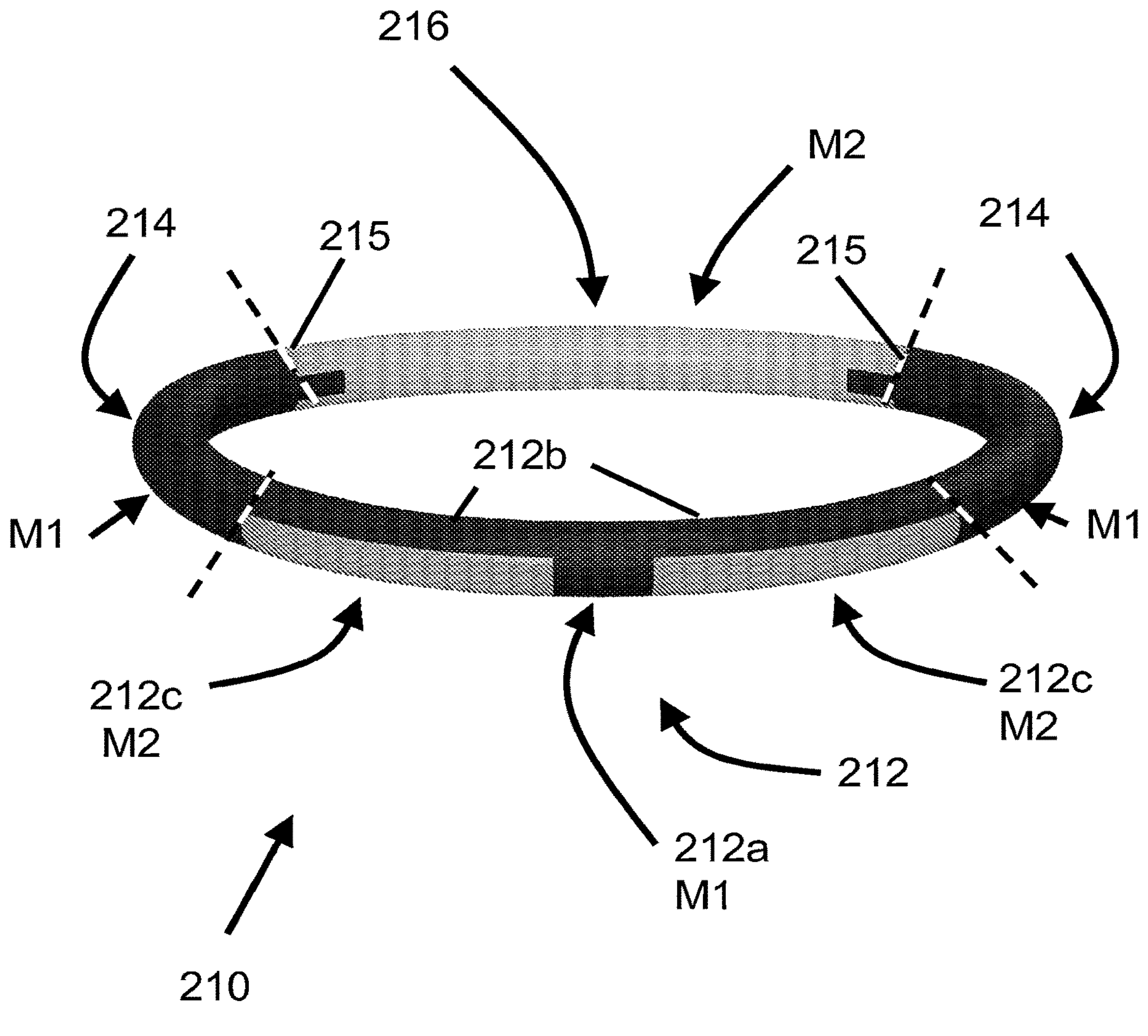
FIGS. 6A-6C show an example of a "D" shaped annuloplasty ring device including a posterior segment, lateral segments, and an anterior segment.
Figure 6B:
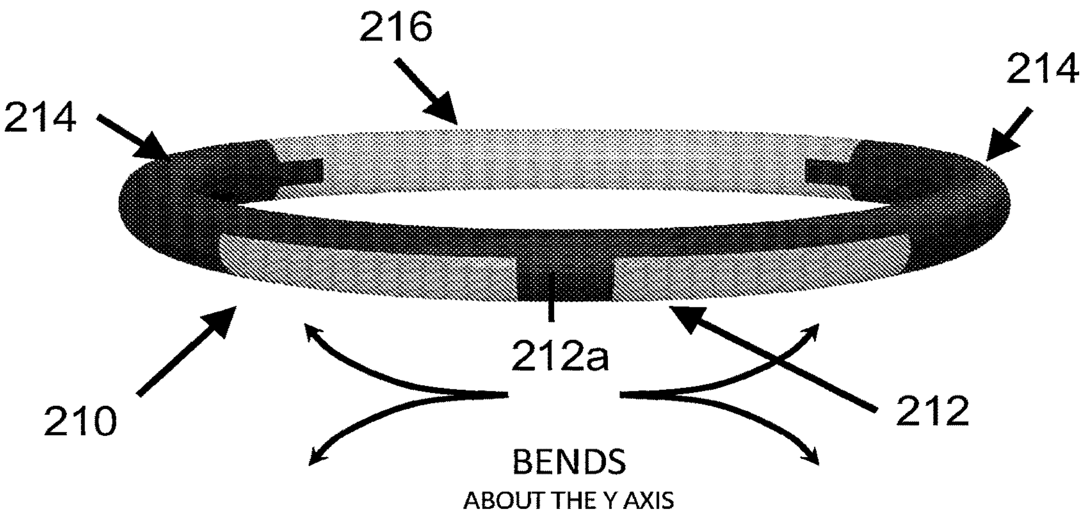
Figure 6C:
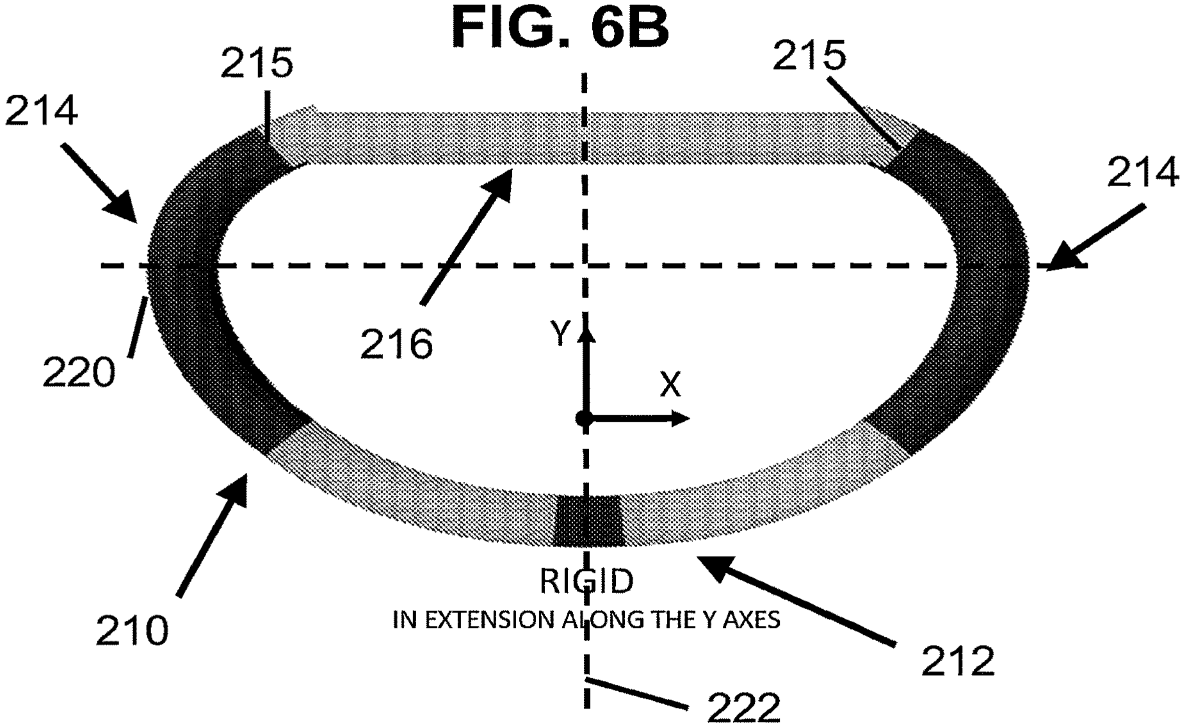

Turning to FIGS. 6A-6C, another example of an annuloplasty device 210 is shown that includes a first structure formed from first material M1 (e.g., represented by the darker color), e.g., that includes an elongate curved posterior segment 212, and first and second curved lateral segments 214 extending from opposite ends of the posterior segment, e.g., generally similar to other devices herein. As shown, the posterior segment 212 and lateral segments 214 lie within a plane (e.g., X-Y plane shown in FIG. 6C), although the segments may have other shapes also generally similar to other examples herein.

In addition, the device 210 includes a substantially straight anterior segment 216 formed from second material M2 (represented by the lighter color) extending between ends of the lateral segments 214 opposite the posterior segment 212 such that device 210 defines a generally "D" shape within the X-Y plane. Similar to other devices herein, as shown in FIG. 6C, the device 210 defines a first lateral axis 220 extending between the lateral segments 214 within the X-Y plane (parallel to the X-axis shown in FIG. 6C), and a second posterior-anterior axis 222 perpendicular to the first axis 220 intersecting a midpoint of the posterior segment 212 (parallel to the Y-axis).

Figure 6D:
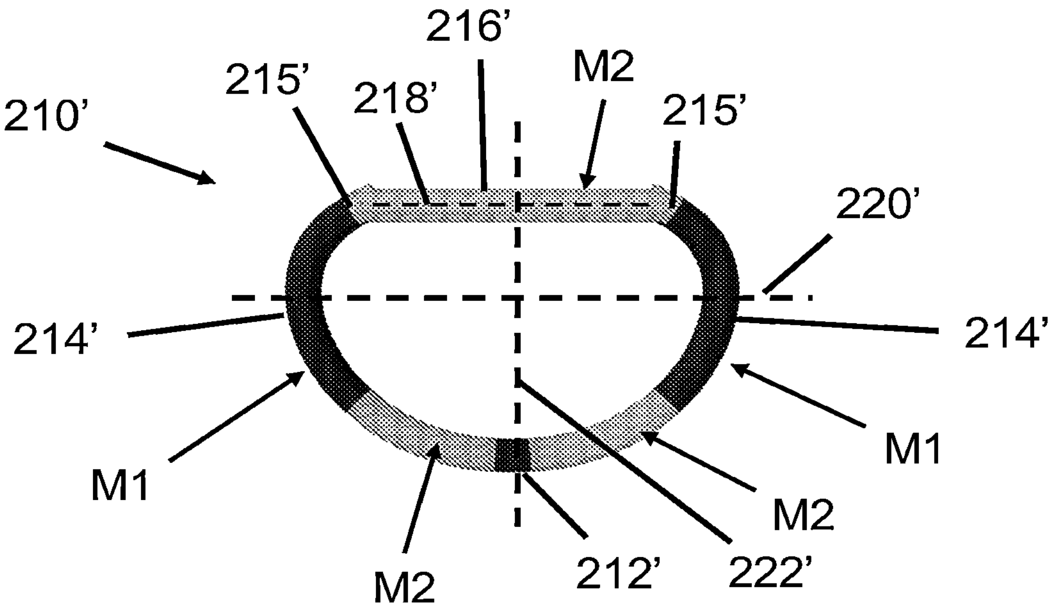
FIGS. 6D and 6E show an alternative to the device of FIGS. 6A-6C including an inelastic filament embedded in the anterior segment.
Figure 6E:
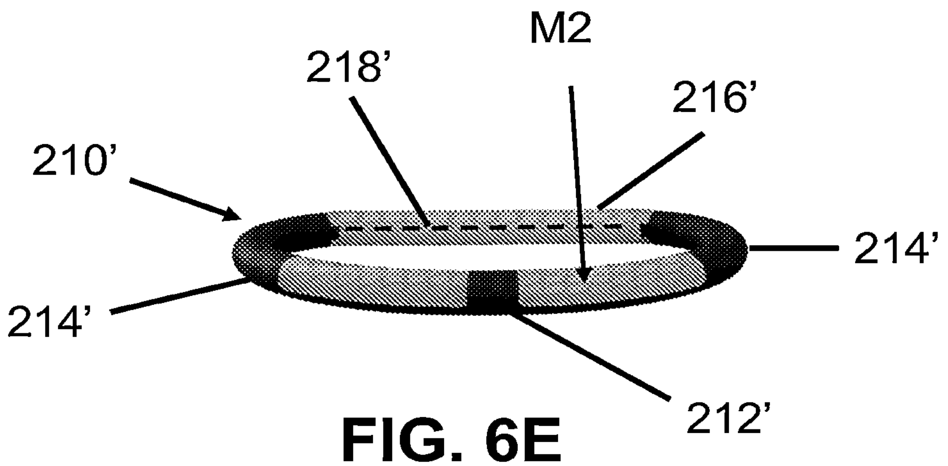

The first material M1 may have a desired first hardness to provide a structure that resists anterior-posterior motion along the second axis 222 within the X-Y plane (as shown in FIG. 6C) while allowing flexibility of the lateral segments 214 to bend out of the X-Y plane about the second axis 222 (as shown in FIG. 6B), e.g., having a hardness ranging from about 50 A to 100 A, e.g., similar to other devices herein. The second material M2 has a second hardness less than the first material, e.g., ranging from about 10 A to 40 A, to provide a flexible and/or elastic anterior segment 216. Optionally, turning to FIGS. 6D and 6E, a similar device 210' is shown that includes an inelastic filament 218', e.g., a suture and the like, may be embedded within the anterior segment 216', e.g., extending between the anterior ends 215' of the lateral segments 214' to provide flexibility in the anterior segment 216' along the second axis 222, e.g., to accommodate movement due to an aortic valve adjacent a mitral valve repaired using the device 210 (not shown), while preventing elongation of the anterior segment 216 along the first axis 220, e.g., to prevent the lateral segments 214' from moving away from one another along the first axis 220.

Optionally, as best seen in FIG. 6A, the posterior segment 212 includes a central region 212*a* spaced substantially midway between the lateral segments 214 that includes a cross-section that is greater than transition regions 212*b* of the posterior segment 212 extending from the central region 212*a* to each of the lateral segments 214. For example, the central region 212*a* may have a substantially circular or oblong cross-section, e.g., similar to the lateral segments 214, while the transition regions 212*b* have thicknesses or heights (perpendicular to the X-Y plane) that are smaller than the height of the lateral segments 214.

For example, the transition regions 212*b* may define a semi-circular or less than semi-circular cross-section, similar to device 10, e.g., defining only a portion of the circular/oblong cross-section of the lateral segments 214, e.g., to provide a desired flexibility to accommodate movement of the lateral segments 214 out of the X-Y plane. In addition or alternatively, the posterior segment 212 may be kerfed or grooved (not shown), similar to other examples herein, to provide desired flexibility in the posterior segment 212.

Thus, in this example, the transition regions 212*b* of the posterior segment 212 have a cross-section defining a maximum width, e.g., a flat surface parallel to the X-Y plane, and a maximum height perpendicular to the maximum width, e.g. defined by a curved surface, that is smaller than the maximum width (and the cross-section of the lateral segments 214). In addition, the posterior segment 212 may include additional material 212*c* attached to the posterior segment 212, i.e., along the transition segments 212*b* having a hardness less than the material of the posterior segment 212 itself. For example, as shown, the transition segments 212*b* may include material 212*c*, which may be material M2 similar to the anterior segment 216, e.g., to may provide a substantially circular or oblong cross-section between along the transition regions 212*b*, optionally, to provide a substantially uniform cross-section for the entire device 210. The softer hardness of the material M2 may be selected to minimize impact on the reduced stiffness of the transition regions 212*b* of the posterior segment 212 and/or may absorb energy to prevent forces from concentrating at edges of the posterior segment 212 while the lateral segments 214 move, as described elsewhere herein. In one example, material M1 may be a relatively stiff polyurethane, e.g., to provide anterior-posterior rigidity, and material M2 may be a flexible polyurethane, e.g., to provide lateral bending, flexibility, and/or energy absorption, e.g., having stiffnesses similar to materials described elsewhere herein. For example, the materials may be selected to provide enhanced biomimicry simulating natural bending properties of tissue of a healthy native valve annulus.

The device 210 may be manufactured in a variety of ways, e.g., to integrate the materials M1, M2 of the device 210. For example, the posterior and lateral segments 212, 214 may be initially formed from first material M1, e.g., by one or more of molding, casting, additive manufacturing, and the like, and then the anterior segment 216 and/or material 215 from second material M2 may be subsequently attached to the first material, e.g., by one or more of over-molding, bonding, coating, fusing, adhering, welding, and the like. Alternatively, the two materials may be formed together, e.g., by co-molding, additive manufacturing, and the like. Fabric (an optionally, an intervening soft layer or coating, not shown) may then be applied over the final structure to provide a finished annuloplasty ring.

Figure 7:
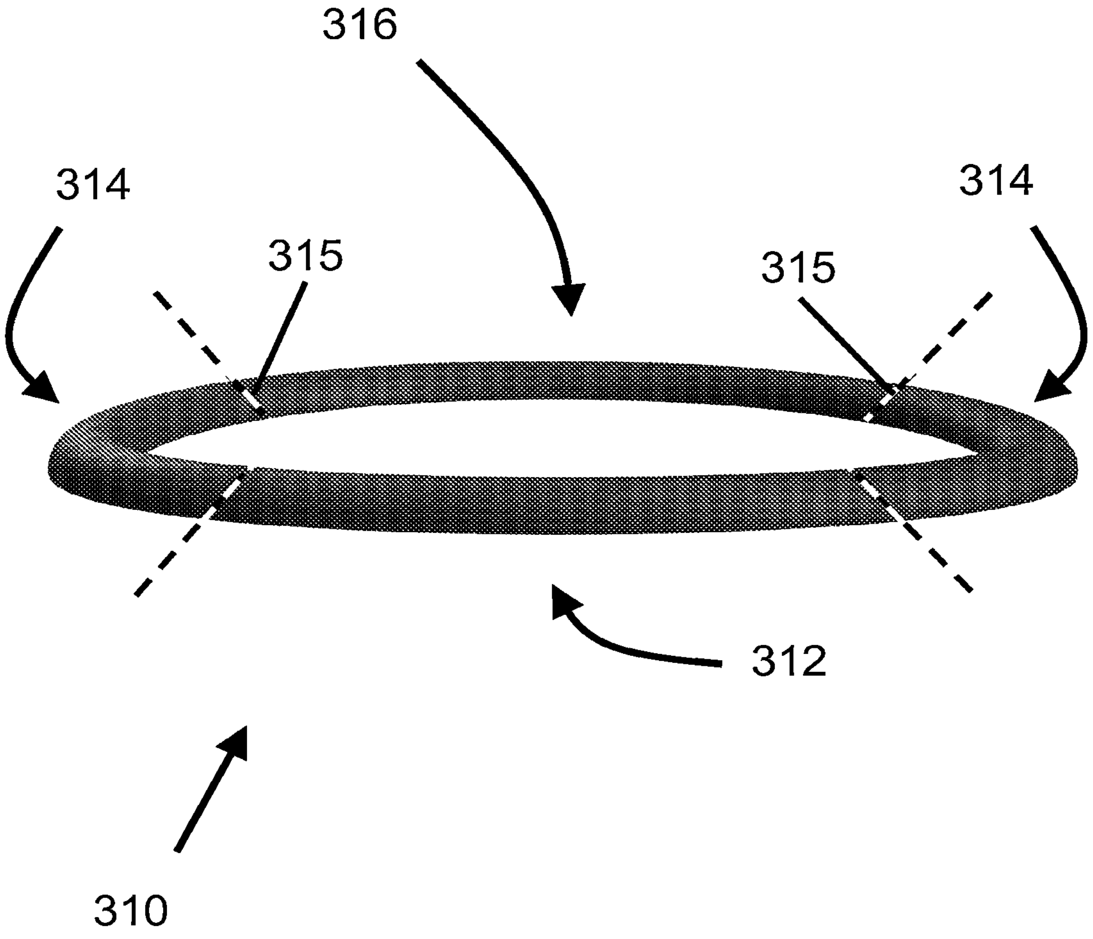
FIG. 7 shows another example of a "D" shaped annuloplasty ring device.

Turning to FIG. 7, another example of an annuloplasty ring device 310 is shown that includes a posterior segment 312 and lateral segments 214, e.g., similar to device 10 shown in FIGS. 3A-3C. In addition, the device 310 includes an anterior segment 316 integrally formed with and extending between anterior ends 315 of the lateral segments 314 opposite the posterior segment 312.

The anterior segment 316 may have a cross-section similar to the posterior and lateral segments 312, 314, e.g., such that the device 310 has a substantially uniform cross-section around the entire device 310. For example, the device 310 may have a substantially flat lower surface that extends around the entire perimeter of the device 310 and a curved upper surface, e.g., defining a semi-circular or less than semi-circular cross section that extends around the entire perimeter. Optionally, in the device 410 shown in FIG. 8, an additional material, e.g., material M2 may be attached to the device 410, e.g., to the flat lower surface to provide a desired final profile and/or to distribute forces in a desired manner through the device 310. For example, the upper region of the device 410 may be formed from more rigid, structural material M1 and softer material M2 may be attached or integrated with the material M1, similar to other devices herein. Although the devices 310, 410 are shown having uniform widths and heights, it will be appreciated that the widths and/or heights (and/or cross-sectional shape) may be varied around the perimeter of the devices 310, 410, as desired to provide desired performance characteristics, and/or may include other features, similar to those described with reference to other devices herein.

Any of the annuloplasty devices herein may be implanted within a patient's heart, i.e., to a mitral valve, using conventional open or minimally invasive procedures. For example, using the device 210 of FIGS. 6A-6C as an example, the anterior segment 216 may be stitched or otherwise secured between trigones on a native mitral valve annulus and the posterior segment 212 secured to the posterior annulus, e.g., shown in FIGS. 1 and 2.

The posterior segment 212 has substantial rigidity in the direction along the poster-anterior axis 212 (e.g., the Y-axis shown in FIG. 1)) such that each endpoint of the anterior segment 210 does not move substantially when the device 210 is subjected to the stress imparted thereon after implantation in the mitral valve annulus of an operating human heart. Additionally, the posterior segment 212 has substantial flexibility around the Y-axis such that the posterior segment 212 may bend to form a parabolic or a hyperbolic shape when device 210 is subjected to the stress imparted thereon after implantation in the mitral valve annulus of an operating human heart, e.g., to accommodate the shape of the mitral valve shown in FIG. 2.

Figure 2:
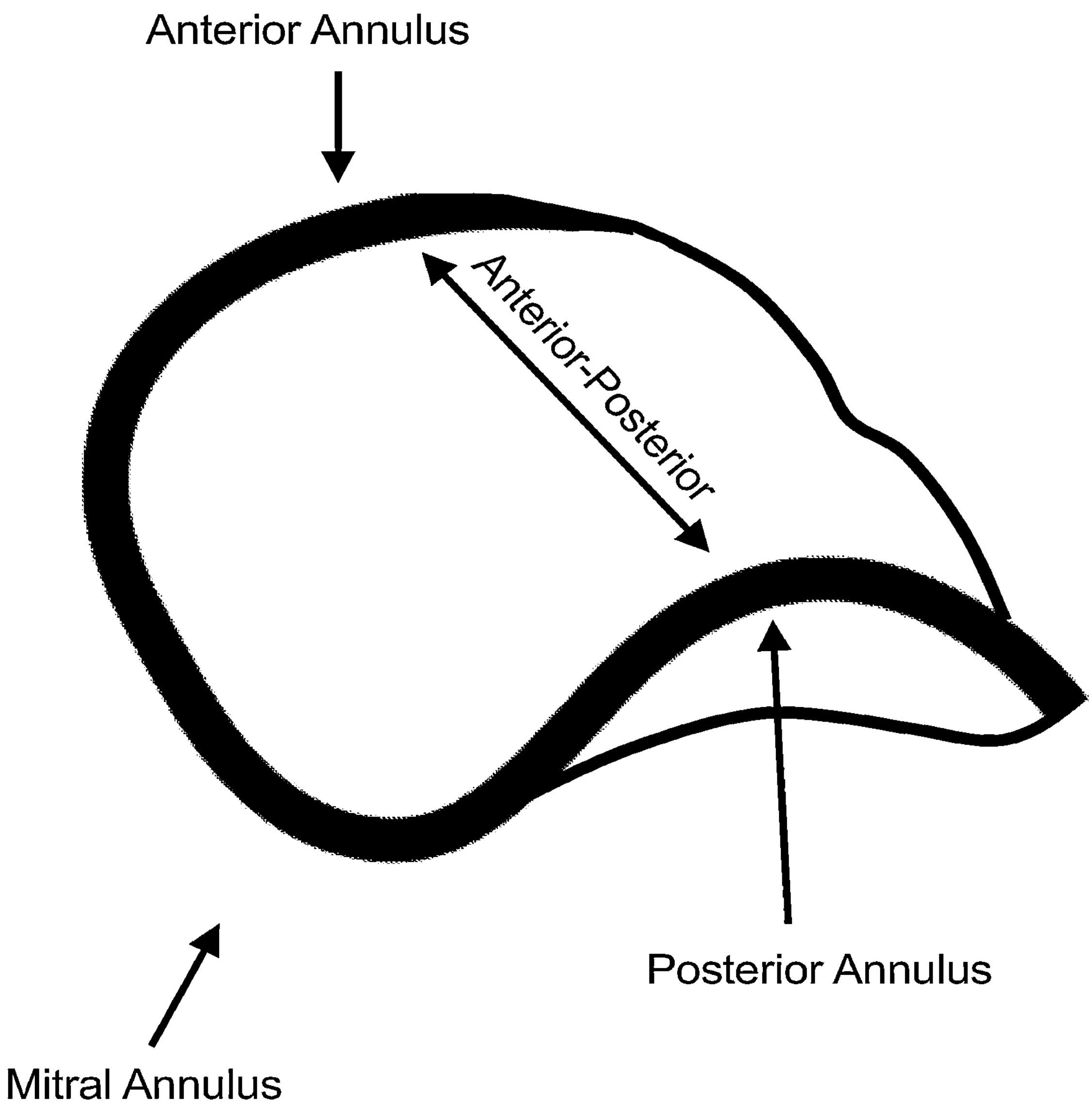

For example, when implanted, the annuloplasty ring devices herein may restrict anterior-posterior dilation of the native mitral valve annulus while allowing for significant conformational changes of the annulus. In particular, the annulus may be able to shift from a relatively flat, planar shape to a three-dimensional saddle shape during a cardiac cycle, e.g., as shown in FIG. 2. Alternatively, the annulus is able to shift from a flatter saddle shape to a steeper saddle shape. In the examples where the anterior segment is flexible or nonexistent, the anterior portion of the mitral valve annulus is able to conform with the natural motion of the anterior annulus, which is impacted by the aorta and aortic valve.

With additional reference to FIGS. 6A-6D, in the example of the device 210, the posterior segment 212 has substantial rigidity in the direction of the second axis 222 (parallel to the Y-axis) defined by a line connecting a centroid of the posterior segment 212 (e.g., at location 212*a*) and a centroid of the anterior segment 216, such that each endpoint of the anterior segment 216 is not substantially separated from the centroid 212*a* of the posterior segment 212 when the device 210 is subjected to the stress imparted thereon after implantation in the mitral valve annulus of an operating human heart.

Additionally, the posterior segment 212 has substantial flexibility around the second axis 222 such that the posterior segment 212 bends to form a parabolic or a hyperbolic shape when device 210 is subjected to the stress imparted thereon after implantation in the mitral valve annulus of an operating human heart. The bending can be envisioned with respect to the native annulus shown in FIG. 2, with the posterior segment 212 bending around centroid 212*a* and around the second axis 222 (as represented by arrows in FIG. 6B).

The anterior segment 216 may be made of a flexible and/or elastic material that allows for the conformational changes of the anterior region of the native annulus. For example, when the device 210 is deformed from its substantially flat shape to a saddle shape, e.g., corresponding to the device 210 adopting the shape of the native annulus as shown in FIG. 2, the overall width of the device 210 (along the first axis 220) may decrease by between about twenty and one hundred percent (20-100%) or between about fifty and eighty percent (50-80%), and the anterior segment 216 may have sufficient flexibility and/or elasticity to accommodate this movement. This motion is relative to the overall annulus motion which both undergoes general conformational changes as well as translates and rotates over the course of a cardiac cycle. In an example, the anterior segment 216 in its resting (unstressed) state is a substantially straight line as shown in FIG. 6C. Alternatively, the anterior portion 216 may have a three-dimensional shape in its resting state and/or other nonlinear shape along its length (not shown). In another alternative example, the anterior segment 216 may include a component that is flexible, but stiff under tension (for instance, PTFE), such that anterior annulus motion is generally permitted, but the distance between the endpoints of the anterior segment 216 does not substantially increase when subjected to the stresses imparted thereon after implantation in the mitral valve annulus of an operating human heart.

Alternatively, the anterior segment 216 may be omitted, and the anterior ends 215 of the lateral segments 214 may be securable to respective native mitral trigones, and the portion of the valve annulus between the trigones is relatively free to undergo conformational changes. It is noted that, in this alternative, the other segments of device 210 may still function to limit the anterior-posterior dilation of the native mitral valve. Additionally, the anterior segment 210 may include a geometry that provides selective flexibility in a comparable manner to that described below for posterior segment 212.

The posterior and lateral segment 212, 214 may function to prevent anterior-posterior dilation of the mitral valve, while permitting conformational changes of the valve annulus. More specifically, when properly implanted into the mitral valve, these segments resist an increase in the distance along the second axis 222 (parallel to the Y-axis) from the native mitral valve trigones to the center of the posterior section of the native annulus.

In one example, the posterior and lateral segments 212, 214 have substantial rigidity in the direction of the second axis 222. For example, the distance traveled/flexed may not be increased by more than two millimeters (2.0 mm) when subjected to a load of five Newtons (5 N) along the second axis 222. Alternatively, or additionally, the distance may not be increased by more than one millimeter (1.0 mm) when subjected to a load of one Newton (1 N) along the second axis 222.

Figure 8:
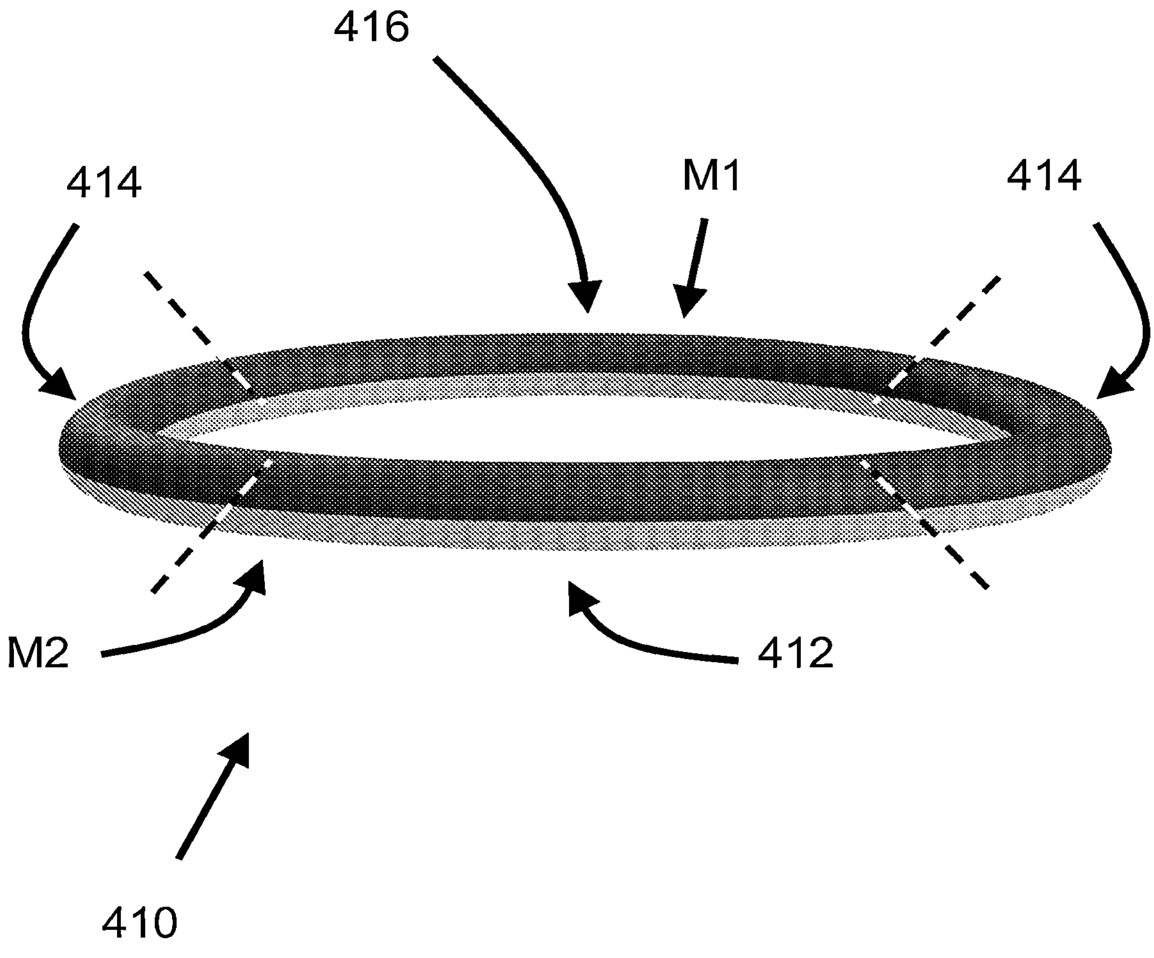
FIG. 8 shows yet another example of a "D" shaped annuloplasty ring device.

The posterior segment 212 may also function to provide flexibility around the second axis 222 such that the posterior segment 212 bends to form a parabolic or hyperbolic shape when the device 210 is subjected to the stress imparted thereon after implantation in the mitral valve annulus of an operating human heart. In one example, this is achieved by the posterior segment 212 having two different layers of material as shown in FIG. 6A or 8, i.e., M1 (top layer) and M2 (bottom layer), respectively. It is noted that in one variation, the relatively thick midpoint 212*a* of the posterior segment 212 may be eliminated. In another variation, the midpoint 212*a*, as shown, may assist in providing desired parabolic or hyperbolic movement of the device 210, e.g., to prevent the posterior segment 212 from buckling or bending in a sharp "V" shape. It will be appreciated that other structural variations may be used to achieve this movement/flexibility, such as, having a plurality of relatively thick regions, similar to midpoint 212*a* with a similar, different and/or varying width aspects, material hardness and/or geometry than as shown in FIG. 6A.

Although the devices described above have been identified for use in mitral valve repair, it will be appreciated that the devices may have other shapes, e.g., partially or enclosed circular or oblong shapes such that the devices may be implanted to repair other structures, such as tricuspid, aortic, or pulmonary valves.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An annuloplasty device, comprising:

a structure comprising an elongate curved posterior segment, first and second curved lateral segments extending from opposite ends of the posterior segment, and a substantially straight anterior segment extending between anterior ends of the lateral segments opposite the posterior segment, the posterior segment, anterior segment, and lateral segments lying within a plane in a resting state, the structure defining a first lateral axis extending between the lateral segments within the plane, and a second posterior-anterior axis perpendicular to the first axis intersecting a midpoint of the posterior segment, wherein the anterior segment is formed from material having a durometer less than material of the posterior and lateral segments such that the structure has a stiffness such that the structure resists anterior-posterior motion along the second axis within the plane while allowing flexibility of the lateral segments out of the plane about the second axis.

2. The device of claim 1, wherein the posterior segment has a cross-section defining a maximum width parallel to the plane and a maximum height perpendicular to the maximum width, the maximum height being smaller than the maximum width to provide directional stiffness wherein the stiffness within the plane is greater than the stiffness out of the plane.

3. The device of claim 1, wherein the lateral segments have the same cross-section as the posterior segment.

4. The device of claim 1, wherein the lateral segments have a substantially circular or oblong cross-section having a maximum width that is greater than the maximum width of the posterior segment.

5. The device of claim 1, wherein the posterior segment and lateral segments have a substantially uniform cross-section.

6. The device of claim 1, wherein the posterior segment includes a central region spaced substantially midway between the lateral segments that includes a cross-section that is greater than regions of the posterior segment extending from the central region to each of the lateral segments.

7. The device of claim 1, wherein the posterior segment is kerfed or grooved to provide flexibility in the posterior segment to facilitate the lateral segments moving out of the plane about the second axis.

8. The device of claim 1, wherein the device defines a generally "D" shape within the plane.

9. The device of claim 1, further comprising an inelastic filament embedded within the material of the anterior segment and extending between the anterior ends of the lateral segments to provide flexibility in the anterior segment along the second axis while preventing elongation of the anterior segment along the first axis.

10. The device of claim 1, wherein the posterior segment includes a central region spaced substantially midway between the lateral segments that includes a cross-section that is greater than regions of the posterior segment extending from the central region to each of the lateral segments.

11. The device of claim 1, wherein the posterior segment is kerfed or grooved to provide flexibility in the posterior segment to facilitate the lateral segments moving out of the plane about the second axis.

12. The device of claim 1, wherein the posterior segment has a cross-section defining a maximum width parallel to the plane and a maximum height perpendicular to the maximum width, the maximum height being smaller than the maximum width to provide directional stiffness wherein the stiffness within the plane is greater than the stiffness out of the plane.

13. The device of claim 12, wherein the lateral segments have a substantially circular or oblong cross-section having a maximum width that is greater than the maximum width of the posterior segment.

14. An annuloplasty device, comprising:

a structure comprising:

an elongate curved posterior segment;

first and second curved lateral segments extending from opposite ends of the posterior segment, the posterior segment and lateral segments lying within a plane; and an anterior segment extending between ends of the lateral segments opposite the posterior segment such that structure defines a generally "D" shape within the plane, wherein the structure defines a first lateral axis extending between the lateral segments within the plane, and a second posterior-anterior axis perpendicular to the first axis intersecting a midpoint of the posterior segment, and wherein the anterior segment is formed from material having a durometer less than material of the posterior and lateral segments such that the structure has a stiffness such that the structure resists anterior-posterior motion along the second axis within the plane while allowing flexibility of the lateral segments out of the plane about the second axis.

15. A method for performing annuloplasty, comprising:

implanting an annuloplasty device within a patient's heart to a mitral valve annulus, the device comprising a posterior segment, lateral segments extending from opposite ends of the posterior segment, and an anterior segment extending between ends of the lateral segments opposite the posterior segment, the posterior segment, lateral segments, and anterior segment lying within a plane, wherein the anterior segment is formed from material having a durometer less than material of the posterior and lateral segments such that the device has a stiffness that resists anterior-posterior motion relative to the valve annulus while allowing flexibility of the lateral segments to follow movement of lateral regions of the valve annulus during normal operation of the heart.

16. The method of claim 15, wherein implanting the annuloplasty device comprises securing the lateral segments to respective trigones of the valve annulus such that the posterior segment extends along a posterior region of the valve annulus.

17. The method of claim 15, wherein the device defines a first lateral axis extending between the lateral segments within the plane, and a second posterior-anterior axis perpendicular to the first axis intersecting a midpoint of the posterior segment, and wherein the posterior segment has substantial rigidity in the direction along the second posterior-anterior axis such that each endpoint of the anterior segment does not move substantially when the device is subjected to the stress imparted thereon after implantation in the mitral valve annulus of an operating human heart.

18. The method of claim 17, wherein the posterior segment is flexible around the second posterior-anterior axis such that the posterior segment bends to form a parabolic or a hyperbolic shape when device is subjected to stress imparted thereon after implantation in the mitral valve annulus of an operating human heart.

19. The annuloplasty device of claim 14, wherein the posterior segment, anterior segment, and lateral segments lying within the plane in an unstressed, resting state.

* * * * *